(12) United States Patent  
Sun et al.

(10) Patent No.: US 6,770,287 B1  
(45) Date of Patent: Aug. 3, 2004

(54) BIOCIDAL CELLULOSIC MATERIAL

(75) Inventors: Gang Sun, Davis, CA (US); Xiangjing Xu, Davis, CA (US); Dean Cliver, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/596,808

(22) Filed: Jun. 19, 2000

(51) Int. Cl.[7] ............................................... A01N 25/34
(52) U.S. Cl. .................... 424/404; 424/76.4; 424/405; 515/326; 252/106; 252/107; 8/189; 8/115.51; 8/115.7; 8/190
(58) Field of Search .............................. 424/404, 76.4, 424/405; 514/376; 252/106, 107; 8/189, 115.51, 115.7, 190

(56) References Cited

U.S. PATENT DOCUMENTS

| | | | |
|---|---|---|---|
| 3,401,005 A | | 9/1968 | Katz |
| 4,844,891 A | * | 7/1989 | Rosen et al. ................ 424/76.4 |
| 5,882,357 A | | 3/1999 | Sun et al. ........................ 8/189 |
| 5,902,818 A | * | 5/1999 | Worley et al. ............... 514/376 |
| 6,077,319 A | | 6/2000 | Sun et al. ........................ 8/189 |
| 6,124,350 A | | 9/2000 | Gagliani et al. |
| 6,162,452 A | * | 12/2000 | Worley et al. ............... 424/405 |
| 6,241,783 B1 | * | 6/2001 | Sun ................................ 8/189 |

\* cited by examiner

Primary Examiner—Yogendra N. Gupta  
Assistant Examiner—D G Hamlin  
(74) Attorney, Agent, or Firm—Townsend and Townsend and Crew LLP

(57) ABSTRACT

The present invention provides, inter alia, durable and renewable biocidal wooden materials for safe food contact items, such as cutting boards and containers, to be used in home kitchens and the food processing industries. The biocidal food contact surfaces of the present invention reduce and eliminate cross-contamination of diseases and make the surfaces or wood cutting boards safer to use. The biocidal materials inactivate any microorganisms that are deposited and prevent the materials from building up biofilms.

21 Claims, 5 Drawing Sheets

5,5-Dimethylhydantoin

4,4,5,5-Tetramethyl-2-imidazolidinone

Monomethoxymethyl-5,5-dimethylhydantoin 2,2,5,5-Tetramethyl-4-imidazolidinone Triazine-1,3,5-trione 1,3-Dimethoxymethyl-5,5-dimethylhydantoin

*Fig. 1*

5,5-Dimethylhydantoin

2,2,5,5-Tetramethyl-
4-imidazolidinone

4,4,5,5-Tetramethyl-
2-imidazolidinone

Triazine-1,3,5-trione

Monomethoxymethyl-
5,5-dimethylhydantoin 1,3-Dimethoxymethyl-
5,5-dimethylhydantoin

CONTROLS

CONTROLS

BLOCK NOS. 15, 28, 10, 16

BLOCK NOS. 18, 24, 12, 14

BLOCK NOS. 22, 27, 7

BLOCK NOS. 6, 13, 23

Fig. 3B

BLOCK NOS. 23, 1, 30, 15

BLOCK NOS. 5, 7, 26, 4

BLOCK NOS. 16, 17, 20, 29

BLOCK NOS. 19, 13, 22, 2

BIOCIDAL CELLULOSIC MATERIAL

RELATED APPLICATIONS

The present application claims priority to U.S. patent application Ser. No. 09/416,203, filed Oct. 8, 1999, now U.S. Pat. No. 6,241,783, which is a continuation-in-part of U.S. patent application Ser. No. 09/102,525, filed Jun. 22, 1998, now U.S. Pat. No. 6,077,319, which is a divisional of U.S. patent application Ser. No. 08/713,406, filed Sep. 13, 1996, now U.S. Pat. No. 5,882,357, the disclosures all of which are hereby incorporated herein by reference in their entirety for all purposes.

BACKGROUND OF THE INVENTION

An important and growing part of the textile industry is the medical and related healthcare and hygiene sectors. Textile materials used in medical-related applications include, for example, surgeon's gowns, caps and masks, patient drapes, bandages, wipers and cover cloths of various sizes. Such textile materials, however, are conductive to cross-infection and transmission of diseases caused by microorganisms. As such, the possibility of spreading infections caused by the lethal HIV virus, the insidious hepatitis virus or other epidemic diseases has created an increased concern regarding the use of protective facilities and uniforms for workers in the medical/healthcare/hygiene sectors. Currently, textile materials used in medical applications are disposable, nonwoven synthetic fabrics that are neither biocidal nor reusable. Such textile fabrics provide protection by blocking the transmission of microorganisms, rather than by inhibiting the growth of the microorganisms. Thus, cross-infection through surface contact of the contaminated textile fabrics is problematic. As a result, in an effort to prevent the cross-infection and transmission of diseases, the contaminated materials must be appropriately sterilized and discarded after use. Unfortunately, such sterilization and discarding procedures result in substantial increases in the cost of healthcare and in the amount of bio-hazardous wastes that are generated.

Accordingly, it is desirable that bacterial infections resulting from contact with contaminated textiles be reduced or eliminated, and that transmission of pathogenic bacteria from person to person during wear or use of contaminated textiles be prevented by inhibiting the growth of the microorganisms on fabrics. Moreover, it is desirable that surgeon's dresses, hospital carpeting and bedding materials, underwear, socks, and uniforms be biocidal so as to provide the best protection possible. In addition, it is desirable to have biocidal textiles for use in, inter alia, hotel-use towels, bedding materials, socks and other hygienic products as well.

Currently, there are two general categories of technologies that can provide protection for medical/healthcare/hygiene personnel. They are (1) physical techniques which involve the formation of a physical barrier against microbial infiltration or transmission by selecting fabric constructions and coating that are impermeable or that are microporous and contain antimicrobial agents; and (2) chemical technologies which involve the incorporation of active functional agents onto fabrics or fibers by grafting or other chemical methods. Disposable materials are examples of the first category. The coating method involves the application of impermeable materials onto the surface of fabrics, thereby blocking the infiltration and permeation of microorganisms. However, cross-infection and spreading of diseases through the contact of the coating surface is still feasible and, thus, pose potential threats to workers who handle the contaminated materials. Moreover, the impermeable properties can cause wearers to become uncomfortable and, in turn, to become less efficient in their.

As such, the chemical association of antibacterial agents onto either the surface or entirety of the material appears to be more practical in terms of durability and efficacy of the antibacterial properties. There are two major pathways to chemically achieve durable antibacterial effects. In one pathway, the slow releasing of biocides through contact with the processed fabrics is employed. In this pathway, a pathway widely used around the world, sufficient chemical agents are impregnated onto the fibers by either chemical or physical methods. Thereafter, the biocides are slowly released from the processed fabrics into the media, thereby contacting and inhibiting the growth of microorganisms. Unfortunately, such chemical agents can be washed away easily if they are not covalently impregnated onto the surface of the fabrics. Moreover, the antibacterial functions are non-regenerable.

In the second pathway, a more innovative technology is employed which involves chemical modification of textile materials with biocidal or potential biocidal compounds, wherein the antibacterial properties of such compounds are regenerable with simple washing. The potential antibacterial groups can be rendered biocidal after washing with certain common chemicals, such as diluted bleaching solutions. Over thirty-five years ago, Gagliardi, et al. first proposed the regeneration principle of antibacterial finishing, hoping to regenerate the lost function by washing the used fabrics with some specific solutions (see, *Am. Dyest. Reptr.*, 51, 49 (1962). However, although much effort has been expended, no commercial products have resulted.

In addition to textiles, food contact articles are another source of bacterial contamination. Multiple outbreaks of foodborne bacterium such as *E. coli* 0157: H7, have made people increasingly conscious of methods to control the spread of such bacterium. Food contact materials such as cutting boards, have long been suspected to be vectors for the spread of foodborne microorganisms. Thus, research has been focused on methods of managing the decontamination of cutting boards as a way to decrease foodborne illness.

Recently, good food hygiene practices as means of preventing foodborne diseases have taken on a new impetus. This is reflected in the USDA move to require safe handling labels on all raw meat and poultry. In the U.S. for example, Salmonella and Campylobacter accounted for 4 million cases annually, while total estimates of gastroenteritis ranged from 6–33 million cases (see, Todd, E., *A Lancet Review*, editors Waites, A. M., and Arbuthnott, J. P., London, pp 9–15, 1991). Although no firm epidemiological data exist as to how many of these result from inappropriate food handling, a researcher indicated that poor handling techniques in kitchens may be responsible for as much as 2–3 million foodborne outbreaks per year (see, Rubino, J., Foodborne Diseases in the Home, Seminar presented at the American Society for Microbiology General Meeting, New Orleans. 1996). Moreover, a recent Dutch report showed that 80% of Salmonella and Campylobacter infections arose from the home (see, Hoogenboom-Verdegaal, A. M. M. et al., *Epidemiol Infect*, 112:481–487. 1994). Considering that the World Health Organization believes that only 10% of actual cases are ever reported, the problem is indeed immense.

About 84% of all foodborne disease were due to bacteria and viruses, causing 9,000 deaths and costing $23 billion to the U.S. economy per year (see Rubino, supra). In Europe, it is estimated that between 50–80% of foodborne outbreaks occur at home (see, Sockett, P. N., *In Encyclopedia of Food Science, Food Technology and Nutrition*, ed. Macrae, R., Academic Press, London, pp. 2023–2031, 1993). One study showed that consumer knowledge of food preparation hygiene was very necessary. The occurrence of foodborne disease is on the rise; and in the developed countries at least, the majority of the salmonellosis and campylobacteriosis is occurring within the home—mostly due to inadequate food hygiene (see, Klontz et al., *J Food Prot.*, 58:927–930. 1995).

Studies also indicate that of all of the causes that were involved, cross-contamination accounted for ~30%, inadequate heating ~45%, and inappropriate storage ~40% (see, Rubino, supra). Studies in the UK showed that cross-contamination was responsible for 14% of human salmonellosis (see, Roberts, D. F., *In Proceedings of the* 2nd World Congress Foodborne Infections and Intoxications 1, Berlin, pp. 157–159. 1986). Indeed, it has become clear that this mode of contamination is much more serious than was previously thought and that the problem is indeed acute not only in the home but also in commercial food processing.

Sites and surfaces as vehicles of cross-contamination have been studied, particularly in Great Britain. In a British survey, moist areas such as the kitchen sink, waste traps and counter tops, as well as dishcloths and sponges, contained large numbers of enteric bacteria (see, Scott et al., *J Hygiene, Cambridge*, 89, 279–293. 1982). Preparation surfaces such as cutting boards were also implicated, containing and spreading pathogens even after washing and cleaning. Serological studies in outbreaks of infant salmonellosis often revealed the same serotype in all members of the family (see, Humphrey et al., *Epidemiol Infect.* 113:402–409 1994).

The main concern with food contact surfaces such as cutting boards is cross-contamination by foodborne or waterborne pathogens from all sources. Although the USDA, FDA, and National Sanitation Foundation allow use of closely grained hardwood for cutting boards, they recommend that plastic cutting boards be used in the kitchen because wooden boards are allegedly harder to decontaminate than plastic, due to wood's inherent porosity. However, this recommendation may be too simplistic. Inherent characteristics of wood such as its superior grip, feel, and forgiveness to wear and tear on knife-edges make it attractive to users and preferable to plastic.

In view of the foregoing, there exists a need in the art for biocidal food contact materials and articles. The present invention remedies such need by providing, inter alia, biocidal food contact materials, surfaces and articles. The biocidal food contact surfaces reduce and eliminate cross-contamination of diseases and make wood surfaces safer. The biocidal surfaces inactivate microorganisms, keep the surfaces free of germs, as well as preventing the materials from building up biofilms.

SUMMARY OF THE INVENTION

The present invention provides, inter alia, durable and regenerable microbiocidal textiles and methods for preparing the same. Such textiles can be readily prepared using a classical wet finishing process to covalently attach a heterocyclic N-halamine to a cellulose based material or other polymeric material. Once prepared, the textiles of the present invention have a broad spectrum of biocidal activity against pathogenic microorganisms. Moreover, the biocidal activity of such textiles can be regenerated by washing with a halogenated solution.

In one embodiment, the present invention provides a process for preparing a microbiocidal cellulosic, cellulosic/polyester or polyester textile precursor, the process comprising: (a) immersing a cellulosic, cellulosic/polyester or polyester textile in an aqueous treating solution which comprises a heterocyclic N-halamine, a wetting agent and a catalyst; (b) removing the excess treating solution from the cellulosic, cellulosic/polyester or polyester textile; (c) drying the cellulosic, cellulosic/polyester or polyester textile; (d) curing the dried cellulosic, cellulosic/polyester or polyester textile; (e) washing the cured cellulosic, cellulosic/polyester or polyester textile to remove excess reagents; and (f) drying the treated cellulosic, cellulosic/polyester or polyester textile to remove water.

In another embodiment, the present invention provides a process for rendering a cellulosic, cellulosic/polyester or polyester textile microbiocidal, the process comprising: (a) washing a microbiocidal cellulosic, cellulosic/polyester or polyester textile precursor with a halogenated solution, the microbiocidal textile precursor being prepared in accordance with the above method; and (b) drying the treated microbiocidal cellulosic, cellulosic/polyester or polyester textile to remove water. In the process, the halogenated solution can be a chlorine solution or, alternatively, a bromine solution. In a presently preferred embodiment, the halogenated solution is a chlorine solution (e.g., a chlorine bleach solution such as Clorox). The washing of the microbiocidal cellulosic, cellulosic/polyester or polyester textile precursor with a halogenated solution renders the textile biocidal and, in addition, it sterilizes the textile.

In yet another embodiment, the present invention provides a composition for finishing fabrics, i.e., an aqueous treating solution, the composition comprising a wetting agent; and a heterocyclic N-halamine. In a preferred embodiment, the composition further includes a catalyst. In an even more preferred embodiment, the composition further includes additives (e.g., softeners and waterproofing agents) to impart favorable characteristics.

In another aspect, the present invention provides cellulose based composition comprising a cellulosic material; and a heterocyclic N-halamine covalently attached to the cellulosic material. The cellulosic material can be a wood material such as a wood, a wood fabric or a wood pulp. In certain instances, the wood material is a food contact material, surface or article. Various food contact materials, surfaces and articles include, but are not limited to, a plate, cookware, cutlery, a knife, a spoon, a cup, a table, a cutting board, a meat block, a baker's top, a counter top, kitchenware and a floor. In a preferred aspect, the present invention provides durable and renewable biocidal wooden materials for safe food contact items and surfaces, such as cutting boards and containers, to be used in home kitchens and food processing industries.

Myriad applications exists for the microbiocidal textiles, or articles of the present invention. For instance, the microbiocidal textile materials can provide biocidal protective clothing to personnel in the medical area as well as in the related healthcare and hygiene area. In contrast to previously used textiles, the textiles of the present invention are not a barrier to microorganisms, but rather a disinfectant to them. As such, the regenerable and reusable biocidal materials can replace currently used disposable, nonwoven fabrics as medical textiles, thereby significantly reducing hospital maintenance costs and disposal fees. The microbiocidal properties of the textiles of the present invention can be advantageously used for women's wear, underwear, socks, and other hygienic purposes. In addition, the microbiocidal properties can be imparted to paper or carpeting materials to create odor-free and germ-free carpets. Moreover, all germ-free environments, such as required in biotechnology and pharmaceutical industry, would benefit from the use of the microbiocidal textiles of the present invention to prevent any contamination from air, liquid, and solid media.

Other features, objects and advantages of the invention and its preferred embodiments will become apparent from the detailed description that follows.

BRIEF DESCRIPTION OF THE DRAWINGS

FIGS. 3 A–B illustrates an amount of CFU recovered from biocidal blocks (A) 5% biocide and (B)10% biocide.

FIGS. 4 A–B (A) illustrates the recovery of viable bacteria on treated and untreated wood at $10^6$ initial inoculation level; (B) illustrates the recovery of viable bacteria on treated and untreated wood at $10^8$ initial inoculation level.

DETAILED DESCRIPTION OF THE INVENTION AND PREFERRED EMBODIMENTS

Various foodborne bacteria and microorganisms flourish on food contact and preparation materials and articles. If raw meat, poultry, egg dishes and other foods are not separated, these bacteria can cross contaminate each other. Moreover, cutting boards and butcher blocks contaminate various non-separated foods. Various pathogenic bacteria such as Campylobacter, *Escherichia coli* O157:H7, Listeria, Salmonella, Shigella, Vibrio, Yersinia, etc., can spread and cause sickness and even death. The present invention provides biocidal cellulosic based materials useful to combat these pathogens.

As such, the present invention provides a cellulose based composition comprising a cellulosic material; and a heterocyclic N-halamine covalently attached to the cellulosic material. The cellulosic material can be a wood material such as a wood, a wood fabric or a wood pulp. In certain instances, the wood material is a food contact surface, material or article. Various food contact surfaces, materials and articles include, but are not limited to, a plate, cookware, cutlery, a knife, a spoon, a cup, a table, a cutting board, a meat block, a baker's top, a counter top, kitchenware and a floor. In other aspects, the cellulosic material is fabricated into a diaper, napkin, a table cloth, a bandage, a gauze, an underpants, a medical garment, and a surgical garment.

The microbiology of the food contact surface is important in determining the propensity to biohazards from pathogenic microorganisms. Growth of bacteria on surfaces can be expressed in the following processes (see, VanLoosdrect, M. C. M. et al, *Microbiol Rev.* 54 (1):75 1990 and Vigo, T. L., Protective clothing effective against biohazards, *Biotechnology and Bioactive Polymers*, Gebelein, C. and Carraher, C. Eds. 225, Plenum Press. 1994):(1) transport of microorganisms by contact-transmission, diffusion, and others; (2) initial adhesion of the bacteria on the surface; (3) attachment of polymers and fibrils; and (4) formation of microcolonies and biofilm on the surface. Many pathogenic and spoilage bacteria form biofilms on materials commonly used in food processing and home food cooking, such as wood and plastic cutting boards and containers. Thus, the surfaces contaminated by the pathogenic bacteria will be new sources of cross-contamination of diseases. Surprisingly, the biocidal wood materials of the present invention are perfect in eliminating surface cross-contamination and providing safe food-contact surfaces and containers.

In another embodiment, the present invention provides a process for preparing a microbiocidal cellulosic, cellulosic/polyester or polyester textile precursor, the process comprising: (a) immersing a cellulosic, cellulosic/polyester or polyester textile in an aqueous treating solution which comprises a heterocyclic N-halamine, a wetting agent and a catalyst; (b) optionally removing the excess treating solution from the cellulosic, cellulosic/polyester or polyester textile; (c) optionally drying the cellulosic, cellulosic/polyester or polyester textile; (d) optionally curing the dried cellulosic, cellulosic/polyester or polyester textile; (e) optionally washing the cured cellulosic, cellulosic/polyester or polyester textile to remove excess reagents; and (f) optionally drying the treated cellulosic, cellulosic/polyester or polyester textile to remove water. "Heterocyclic N-halamine," as used herein, refers to a 4- to 7-membered ring, wherein at least 3 members of the ring are carbon, and from 1 to 3 members of the ring are nitrogen heteroatom, and from 0 to 1 member of the ring is oxygen heteroatom, wherein from 0 to 2 carbon members comprise a carbonyl group, and wherein at least 1 to 3 nitrogen atoms are substituted with a hydroxyalkyl group, such as —$CH_2OH$, or a alkoxyalkyl group, such as —$CH_2OCH_3$. In addition, the ring members can be further substituted with alkyl groups, such as methyl, ethyl, etc. Heterocyclic N-halamines are generally disclosed in U.S. Pat. No. 5,490,983 issued to Worley, et al. on Feb. 13, 1996, the teachings of which are incorporated herein by reference for all purposes.

Heterocyclic N-halamines suitable for use in accordance with the present invention include, but are not limited to, the following: monomethylol-5,5-dimethylhydantoin (MDMH), 1,3-dimethylol-5,5-dimethylhydantoin (DMDMH); monomethylolated and dimethylolated derivatives of 6,6-dimethyl-1,3,5-triazine-2,4-dione, 4,4,5,5-tetranethyl-1,3-imidazolidin-2-one, cyanuric acid and 5,5-dimethylhydantoin; and monomethoxylated and dimethoxylated derivatives of monomethylolated and dimethylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid, 5,5-dimethylhydantoin and 2,2,5,5-tetramethyl-1,3-imidazolidin-4-one. Examples of the monomethoxylated and dimethoxylated compounds are monomethoxymethyl-5,5-dimethylhydantoin and 1,3-dimethoxymethyl-5,5-dimethylhydantoin, respectively. In a presently preferred embodiment, monomethylol-5,5-dimethylhydantoin and 1,3-dimethylol-5,5-dimethylhydantoin are the heterocyclic N-halamines employed. In another embodiment, the N-halamines disclosed in U.S. patent application Ser. No. 09/535,348, filed Mar. 24, 2000, incorporated herein by reference, are suitable for use in the present invention.

In certain embodiments, the heterocyclic N-halamines used in the present invention are commercially available from a number of different sources. For instance, monomethylol-5,5-dimethylhydantoin (MDMH) and 1,3-dimethylol-5,5-dimethylhydantoin (DMDMH) are commercially available under the tradenames DANTOIN® and GLYDANT® XL-1000, respectively, from LONZA, INC. (Fair Lawn, N.J.). Moreover, cyanuric acid is commercially available from ALDRICH® (Milwaukee, Wis.). In addition, those of skill in the art will readily appreciate that the heterocyclic N-halamines used in the present invention can be synthesized in a variety of ways using conventional synthetic chemistry techniques. In this connection, those of skill will readily appreciate that the dimethoxylated derivatives are prepared from the dimethylated derivatives, whereas the monomethoxylated derivatives are prepared from either the mono- or dimethylated derivatives.

Figure 1:
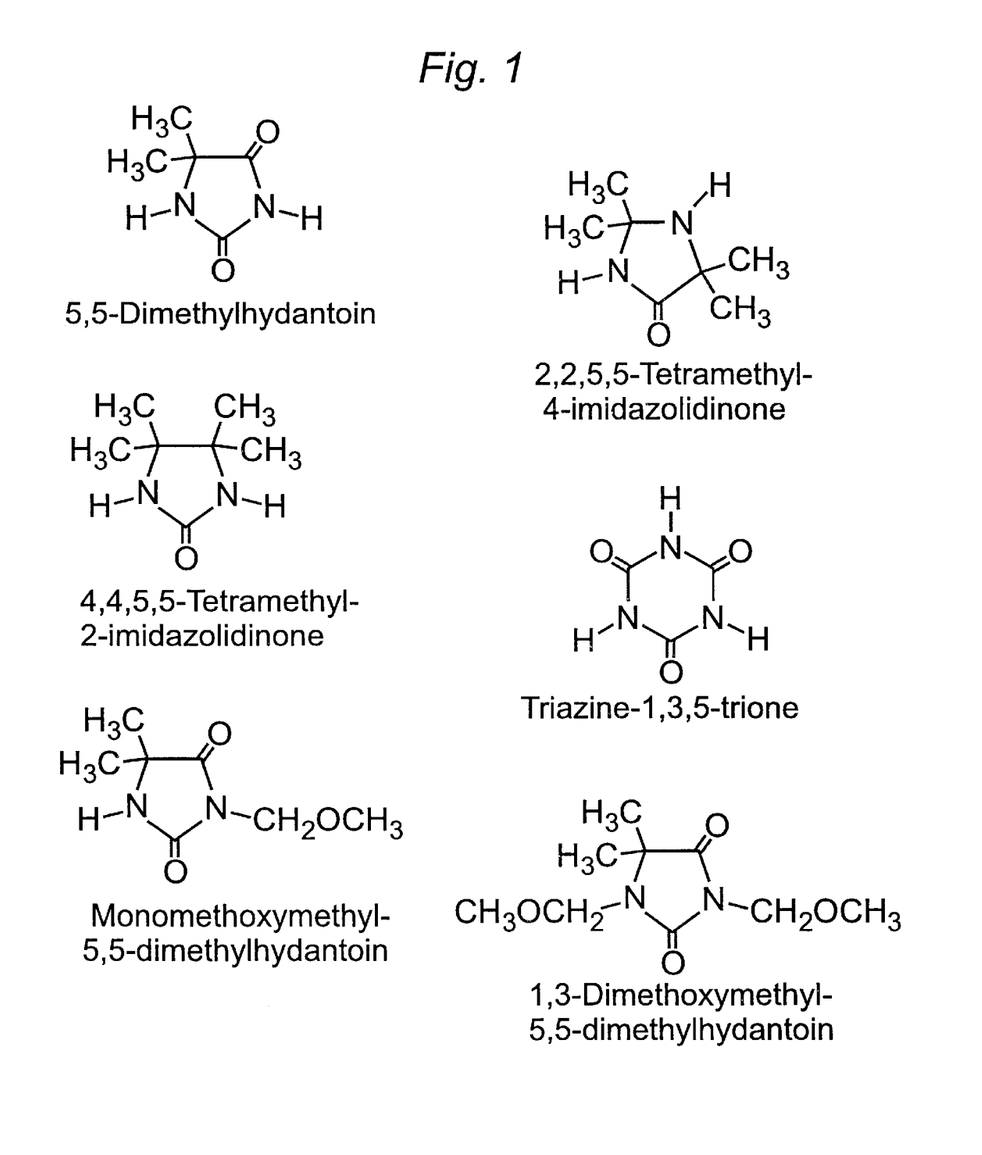
FIG. 1 illustrates examples of heterocyclic N-halamines, which are suitable for use in the present invention.
Figure 2:
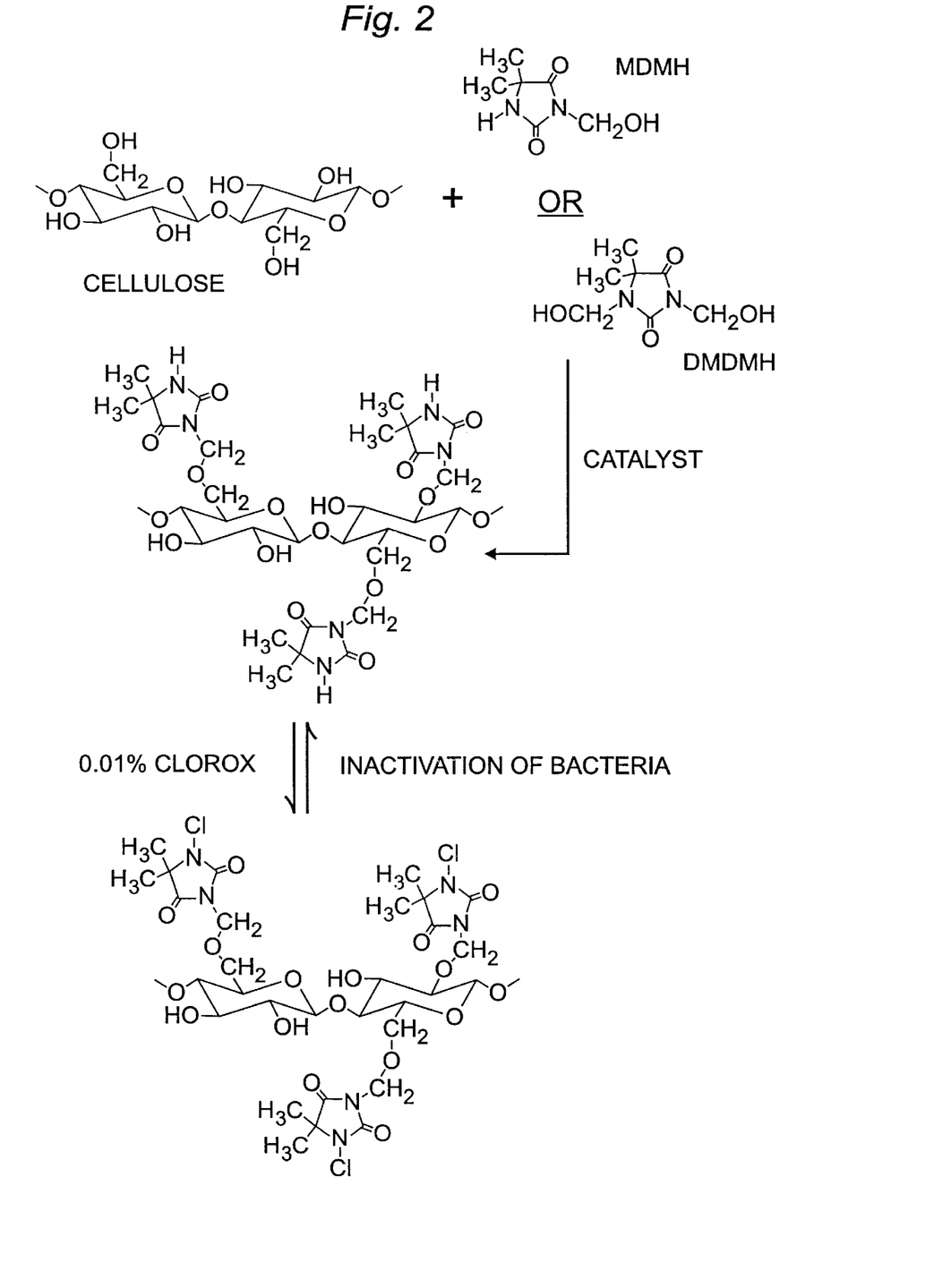
FIG. 2 illustrates the reaction scheme whereby the heterocyclic N-halamine is covalently attached to cellulose.

Examples of heterocyclic N-halamines suitable for use in the present invention are set forth in FIG. 1. It should be noted that many of these heterocyclic N-halamines are widely used in cosmetic products and their halogenated derivatives are major disinfectants for use in, for example, swimming pools. As such, these compounds will not generate any toxic effects for humans or for the environment either in terms of the finished fabric or during the finishing process. "Microbiocidal," as used herein, refers to the ability to kill at least some types of microorganisms, or to inhibit the growth or reproduction of at least some types of microorganisms. The textiles prepared in accordance with the present invention have microbiocidal activity against a broad spectrum of pathogenic microorganisms. For example, such textiles have microbiocidal activity against representative gram-positive (such as *Staphylococcu aureus*) and gram-negative bacteria (such as *Escherichia coli*). Moreover, the microbiocidal activity of such textiles is readily regenerable.

In step (a) of the above process, the aqueous treating solution comprises a heterocyclic N-halamine as described above, a wetting agent and a catalyst. As used herein, "wetting agent" refers to a substance that increases the rate at which a liquid spreads across a surface, i.e., it renders a surface nonrepellent to a liquid. Examples of suitable wetting agents include, but are not limited to, TRITON® X-100 (generically, octylphenoxypolyethoxyethanol) (Sigma Chemical Co., St. Louis, Mo.), SEQUAWET® (generically, a nonionic dispersant) (Sequal Chemical Inc., Chester, S.C.), and AMWET® (generically, a wetting agent, detergent penetrant for textile processing) (American Emulsions Co., Dalton, Ga.). Other wetting agents suitable for use in the present invention will be known to and used by those of skill in the art. As used herein, "catalyst" refers to a substance that augments the rate of a chemical reaction without itself being consumed. Suitable catalysts for use in the present invention include, but are not limited to, the following: magnesium salts, zinc salts and ammonium salts. In a presently preferred embodiment, the catalyst employed is one of the following: $MgCl_2$, $Mg(NO_3)_2$, $Zn(NO_3)_2$ and $NH_4NO_3$.

Those of skill in the art will readily appreciate that the concentration of the various components of the aqueous treating solution can be widely varied depending upon the particular components employed and the results desired. Typically, the heterocyclic N-halamine is present at a concentration of at least about 0.2%. More typically, the heterocyclic N-halamine is present at a concentration ranging from about 0.2% to about 20%, more preferably at a concentration ranging from about 0.5% to about 10% and, more preferably at a concentration ranging from about 1% to about 5%. It will be readily apparent to those of skill in the art that higher heterocyclic N-halamine concentrations (e.g., 50%) can be employed, but such higher concentrations are not required to impart microbiocidal activity. Again, suitable microbiocidal activity can be imparted using a heterocyclic N-halamine concentration as low as about 0.2%. The wetting agent is typically present at a concentration ranging from about 0.1% to about 3% and, more preferably, at a concentration ranging from about 0.2% to about 1%. The concentration of the catalyst employed will depend on the concentration of the heterocyclic N-halamine employed. Typically, the ratio of heterocyclic N-halamine to catalyst present will range from about 10:1 to about 5:1. The pH of the aqueous treating solution will typically range from a pH of about 2 to about 6 and, more preferably, from a pH of about 2.5 to about 4.5.

Those of skill in the art will readily appreciate that other additives can be incorporated into the aqueous treating solution to impart favorable characteristics to the cellulosic, cellulosic/polyester or polyester textile. Such additives can include softeners and waterproofing agents that are known to and used by those of skill in the art. Examples of softeners which can be added to the aqueous treating solution include, but are not limited to, MYKON® and SEQUASOFT®, both of which are commercially available from Sequal Chemical Inc. (Chester, S.C.). Examples of waterproofing agents which can be added to the aqueous treating solution include, but are not limited to, SEQUAPEL® (Sequal Chemical Inc., Chester, S.C.), SCOTCHGARD (3M, St. Paul, Minn.) and other water repellent finishing solutions used by those of skill in the art.

In carrying out step (a), the textile used may be roving, yarn or fabric regardless of whether spun, knit, or woven, or may be nonwoven sheets or webs. Moreover, the textile may be made of cellulosic fibers, polyester fibers or blends of these. In addition, other polymer materials having reactive functional groups (e.g. —OH groups) can be used. Such polymer materials include, but are not limited to, polyvinyl alcohol (PVA), starches and proteins. In wetting the textile in the finishing or treating bath, ordinary textile equipment and methods suitable for batchwise or continuous passage of roving, yarns or fabrics through an aqueous solution may be used, at any speed permitting thorough and uniform wetting of the textile material.

In step (b), the excess aqueous treating solution is removed by ordinary mechanical methods such as by passing the textile between squeeze rolls, by centrifugation, by draining or by padding. In a preferred embodiment, the excess aqueous treating solution is removed by padding.

In step (c), the cellulosic, cellulosic/polyester or polyester textile is dried at a temperature ranging from about 50° C. to about 90° C. and, more preferably, at a temperature ranging from about 75° C. to about 85° C. for a period of time ranging from about 3 to about 8 minutes and, more preferably, for about 5 minutes.

In step (d), the dried cellulosic, cellulosic/polyester or polyester textile is cured at a temperature ranging from about 120° C. to about 180° C. and, more preferably, at a temperature ranging from about 140° C. to about 160° C. for a period of time ranging from about 3 to about 8 minutes and, more preferably, for about 5 minutes. The heating can be carried out in an oven, preferably one having a forced draft of air directed at the surface of the textile and exhausting through a vent to remove fumes.

In step (e), the dried cellulosic, cellulosic/polyester or polyester textile is washed. Washing of the treated textile, step (d), may be done with either hot or cold water. The covalent bonds formed are stable, insoluble, and durable to the mechanical agitation, spraying and rubbing that occurs in washing machines or in large scale continuous or batchwise textile washing equipment.

Final drying, step (f), can be carried out by any ordinary means such as oven drying, line drying or tumble drying in a mechanical clothes dryer. A drying temperature of about 80° to about 120° C. for about 1 to about 5 minutes is particularly preferred.

In another embodiment, the present invention provides a process for rendering a cellulosic, cellulosic/polyester or polyester textile microbiocidal, the process comprising: (a) washing a microbiocidal cellulosic, cellulosic/polyester or polyester textile precursor with a halogenated solution, the microbiocidal textile precursor being prepared in accordance with the above method; and (b) drying the treated microbiocidal cellulosic, cellulosic/polyester or polyester textile to remove water. In the process, the halogenated solution can be a chlorine solution or, alternatively, a bromine solution. In a presently preferred embodiment, the halogenated solution is a chlorine solution (e.g., a chlorine bleach solution such as CLOROX®). The washing of the microbiocidal cellulosic, cellulosic/polyester or polyester textile precursor with a halogenated solution renders the textile biocidal and, in addition, it sterilizes the textile. Moreover, as previously explained, the microbiocidal activity, i.e., oxidative properties, of the textiles can be regenerated by periodically washing the textile with a halogenated solution during regular washings.

In yet another embodiment, the present invention provides a composition for finishing fabrics, the composition comprising a wetting agent; and a heterocyclic N-halamine. In a preferred embodiment, the composition further includes a catalyst. In an even more preferred embodiment, the composition further includes additives (e.g., softeners and waterproofing agents) to impart favorable characteristics. The discussions pertaining to the heterocyclic N-halamines, wetting agents, catalysts, additives and their various concentrations are fully applicable to this composition and, thus, such discussions will not be repeated again. The pH of the aqueous treating solution will typically range from a pH of about 2 to about 6 and, more preferably, from a pH of about 2.5 to about 4.5. Those of skill in the art will readily appreciate that the above composition can be prepared in a concentrated form or, alternatively, in a form suitable for immediate use, i.e., at appropriate reagent concentrations.

Considering both antibacterial and mechanical properties of the finished textiles prepared using the methods and compositions set forth herein, those of skill will readily appreciate that such finished textiles can advantageously be used in the preparation of the following articles: surgeon's gowns, caps, masks, surgical cover, patient drapes, carpeting, bedding materials, underwear, socks, uniforms, etc. Those of skill in the art will readily appreciate that the finished textiles of the present invention can also advantageously be used for a variety of other purposes, such as in hotel-use towels, bedding materials, hygienic products, in various clothing to protect against pesticides and other toxic chemicals, etc.

Using the process of the present invention, the cellulosic material, such as wood, is modified chemically with potential biocidal compounds that are nontoxic and environmentally friendly, and these groups are activated by a halogenated material such as chlorine bleach, following a reversible chemical reaction such as redox reactions. Thus, the durable and regenerable antimicrobial functions are implemented by following the cycle that oxidants will change to their precursor forms after killing bacteria, and then will return to oxidants forms after halogenating (e.g. chlorine-bleaching). As such, a rechargeable cycle is formed in the above way having a mechanism of regeneration of antibacterial function.

In a preferred aspect, precursors of halamines are permanently incorporated onto wood cellulose. Halamine structures are oxidative compounds that have sufficient potential to inactivate a broad spectrum of pathogenic microorganisms. The fundamental chemistry of inactivation of bacteria by halamines can be expressed in the following equation (Equation 1):

Equation 1

Equation 1 illustrates the chemical reaction and mechanism of the biocidal function and the regeneration process. As can be observed from the reaction, an aqueous halogenated solution such as Clorox, is the chemical agent to activate the biocidal functions. Thereafter, the potential biocidal groups grafted on cellulose, e.g. hydantoin derivatives, are converted to biocidal halamine structures. Without being bound by any particular theory, it is believed that the mechanism of killing microorganisms by halamines is a chemical oxidation or a disinfection process, rather than chemotherapy, thus it is non-selective to germs and non-mutable.

In certain embodiments, the present invention provides a process for making a cellulosic material a biocidal article, comprising:

(a) immersing the cellulosic material in an aqueous treating solution which comprises a catalyst, a wetting agent and a heterocyclic amine; and (b) treating the cellulosic material with a halogenated aqueous solution, thereby rendering the cellulosic material biocidal.

In certain aspects of the present invention, several steps can optionally be inserted between step (a) and (b) above. For instance, in certain preferred aspects, the method further comprises removing excess aqueous treating solution from the material before treating the material with a halogenated aqueous solution. In this aspect, the excess aqueous treating solution is removed by ordinary mechanical methods, such as by passing the material (e.g., wood) by draining or by padding. In a preferred embodiment, the excess aqueous treating solution is removed by draining.

In addition, the process optionally further comprises drying the material after removing excess aqueous treating solution to produce a dried material. In this aspect, the material is dried at a temperature ranging from about 50° C. to about 90° C. and, more preferably, at a temperature ranging from about 75° C. to about 85° C. for a period of time ranging from about 3 to about 8 minutes and, more preferably, for about 5 minutes.

Moreover, the dried material can optionally be cured to produce a cured material. The curing process is conducted at a temperature ranging from about 120° C. to about 200° C. and, more preferably, at a temperature ranging from about 140° C. to about 160° C. for a period of time ranging from about 3 to about 8 minutes and, more preferably, for about 5 minutes. The heating can be carried out in an oven, preferably one having a forced draft of air directed at the surface of the material and exhausting through a vent to remove fumes.

The cured material is then optionally washed to remove excess reagents. Washing of the treated material can be done with water. The covalent bonds formed are stable, insoluble, and durable to the mechanical agitation, spraying and rubbing that occurs in washing machines or in large scale continuous or batchwise textile washing equipment. In certain preferred embodiments, the process further comprises drying the washed material to remove water.

The material can optionally be dried before treating the material with a halogenated aqueous solution, to render the material biocidal. Drying of the material, can be carried out by any ordinary means such as oven drying. A drying temperature of about 80° C. to about 120° C. is particularly preferred. Suitable drying times are generally less than 15 minutes in duration.

In certain embodiments, the present invention provides a process for making a cellulosic material a biocidal material, surface or article, comprising:

(a) immersing the cellulosic material, surface or article in an aqueous treating solution which comprises a catalyst, a wetting agent and a heterocyclic amine; (b) removing the excess treating solution from the material, surface or article; (c) drying the material, surface or article; (d) curing the material, surface or article; (e) washing the cured material, surface or article to remove excess reagents; (f) drying the washed material, surface or article to remove water; and (g) treating the cellulosic material, surface or article with a halogenated aqueous solution, thereby rendering the cellulosic material, surface or article biocidal.

The invention will be described in greater detail by way of specific examples. The following examples are offered for illustrative purposes, and are intended neither to limit nor define the invention in any manner.

EXAMPLES

Example I

This example illustrates the finishing of fabrics with monomethylol-5,5-dimethythydantoin (MDH or Anti-1).

A finishing bath containing 24 grams of monomethylol-5,5-dimethyl-hydantoin, 4.8 grams magnesium chloride, and 0.6 gram of Triton X-100 (a wetting agent) in 600 milliliters of deionized water was prepared. The pH of the finishing bath was adjusted to 3.4 with one milliliter of 0.1 N HCl solution. Then, 140.9 grams of pure cotton fabric (#400 Testfabrics, Inc., Middlesex, N.J.) and 141.4 grams of cotton/polyester (35/65) blend fabric (#7409, Testfabrics, Inc., Middlesex, N.J.) were dipped in the bath for more than five minutes and padded through a padder with a more than 80% pick-up rate. The fabrics were dipped and padded again, and dried at 80° C. for 5 minutes. The fabrics were then cured at 160° C. for 5 minutes. Finally, the finished fabrics were machine washed with 90 grams of American Association of Textile Chemists and Colorists (AATCC) Standard Reference Detergent 124 at a low water level and a temperature of about 60° C. for 30 minutes. The fabrics were dried and weighed, yielding 42.8 grams (1.35% add-on) of the cotton fabric and 142.4 grams (0.71% add-on) of the cotton/polyester blend fabric. The cotton product exhibited prominent infrared adsorption bands in a KBr pellet at 1718 and 1770 $cm^{-1}$.

Thereafter, the finished fabrics were washed with a diluted Clorox solution containing about 0.01% active chlorine. Antibacterial properties of the fabrics were tested against representative gram-positive (such as *Staphylococcu aureus* (ATCC 5368)) and gram-negative bacteria (such as *Escherichia coli* (ATCC 2666)) using the protocol set forth in Example III.

Example II

This example illustrates the finishing of fabrics with 1,3-dimethylol-5,5-dimethylhydantoin (DMDMH or Anti-2).

A finishing bath containing 48 grams of 1,3-dimethylol-5,5-dimethylhydantoin (DMDMH or Anti-2), 9.6 grams magnesium chloride and 0.8 gram of Triton X-100 (a wetting agent) in 800 milliliters of deionized water was prepared. The pH of the finishing bath was adjusted to 3.1 with 20 milliliters of 0.01 N HCl solution. Then, 144.7 grams of pure cotton fabric (#400 Testfabrics, Inc., Middlesex, N.J.) and 143.2 grams of cotton/polyester (35/65) blend fabric (#7409, Testfabrics, Inc., Middlesex, N.J.) were dipped in the bath for more than five minutes and padded through a padder with more than an 80% pick up rate. The fabrics were dipped and padded again, and dried at 80° C. for 5 minutes. The fabrics were then cured at 160° C. for 5 minutes. Finally, the finished fabrics were machine washed with 90 grams of AATCC Standard Reference Detergent 124 at a low water level low and a temperature of about 60° C. for 30 minutes. The fabrics were dried and weighed, yielding 147.9 grams (2.22% add-on) of the cotton fabric and 145.5 grams (1.62% add-on) of the cotton/polyester blend fabric. The cotton product exhibited prominent infrared adsorption bands in a KBr pellet at 1718 and 1770 $cm^{-1}$.

Thereafter, the finished fabrics were washed with a diluted CLOROX® solution containing about 0.01% active chlorine. Antibacterial properties of the fabrics were tested against representative gram-positive (such as *Staphylococcu aureus* (ATCC 5368)) and gram-negatibe bacteria (such as *Escherichia coli* (ATCC 2666)) using the protocol set forth in Example III.

Example III

This example illustrates the qualitative antibacterial study of the Anti-1 finished fabrics carried out using the AATCC Test Method 147.

Fabric samples of #405 (pure cotton, Testfabrics, Inc., Middlesex, N.J.) and # 7402 (cotton/polyester 35/65, Testfabrics, Inc., Middlesex, N.J.) were finished in a manner similar to that set forth in Example I. The concentration of the finishing agent used was from about 5 to 15% in the finishing of the cotton fabrics and from about 5 to 20% in the finishing of the cotton/polyester (35/65) blend fabric because of the lower concentration of cellulose in the blend. The final biocidal property was imparted onto the finished fabrics by washing them with a diluted CLOROX® solution containing 0.25% chlorine after each washing circle. Qualitative antibacterial tests were conducted according to AATCC Test Method 147.

In the AATCC Test Method 147, two pieces of chlorinated fabrics with the size of 25 mm×50 mm were placed on a nutrient agar plate which had been inoculated by five streaks of a diluted bacteria solution using a 4 mm inoculating loop. The diluted bacteria solution was prepared by transferring 1.0 milliliter of 24 hour broth culture into 9.0 milliliter of sterile distilled water. The agar plate was incubated at 37° C. for 18–24 hours. The minimum width of inhibition zone along a streak on either side of the test specimen are measured. Table I sets forth the qualitative biocidal evaluations of the finished fabrics with different concentration of the agent Anti-1. Even with a 5% finishing agent concentration and about a 1% add-on of the agents, the processed fabrics exhibit durable and regenerable antibacterial properties.

TABLE I

Results of Finished Cotton (#405) and Cotton/Polyester 35/65 (#7402)

| Fabric | Conc. of Anti-1 (%) | Add-on % | Biocidal Results* After 20 Times Washing | | Biocidal Results After 50 Times Washing | |
|---|---|---|---|---|---|---|
| | | | E. coli | S. aureus | E. coli | S. aureus |
| #405 | 5 | 1.2 | >3 mm | >1 mm | >1 mm | ~1 mm |
| | 10 | 2.3 | >8 mm | >3 mm | >3 mm | >1 mm |
| | 15 | 3.1 | kill all | kill all | >4 mm | >4 mm |
| #7402 | 5 | 0.8 | >3 mm | >1 mm | >1 mm | ~1 mm |
| | 10 | 1.4 | >3 mm | >1 mm | >2 mm | ~1 mm |
| | 15 | 1.6 | kill all | kill all | >2 mm | >1 mm |
| | 20 | 2.0 | kill all | >4 mm | >3 mm | >1 mm |

*Biocidal results were tested with AATCC test method 147, the minimum disinfection distance is measured in millimeter (mm). Washing tests were conducted with machine wash warm according to AATCC test method 124 and AATCC Standard Reference Detergent 124 was used.

Example IV

Four types of clothing materials, i.e., #400, #7402 (35/65 cotton/polyester), Terry cloth and Rayon (all from Testfabrics, Inc., Middlesex, N.J.), were chemically finished with the functional agent following the protocol set forth in Example I. The antibacterial results of the different fabrics finished with Anti-1 are shown in Table II. The percentage of add-on of functional agents by the fabrics was only about 1%. However, after activation of the biocidal properties of the fabrics by washing the fabric with diluted CLOROX®, the zones of inhabitation of bacteria were relatively large. The results indicate that the cellulose-containing materials can easily incorporate with the functional finishing agents and obtain the desired function against microorganisms in a broad spectrum. If complete disinfection is required, the add-on rate of the finishing agents could be increased by increasing the concentration of the agents as discussed above. However, in most applications, only appropriate biocidal properties are needed, especially in the anti-odor finishes.

TABLE II

Antibacterial Results of Different Fabrics Finished with Anti-1

| Fabrics | % Add-on of the agent | Biocidal results against *S. aureus* after being activated (mm) | Biocidal results against *E. coli* after being activated (mm) |
|---|---|---|---|
| Cotton cloth #400 | 1.43 | >1.0 | >2.0 |
| Rayon | 1.21 | >1.0 | >1.0 |
| Dacron/Cotton 65/35 #7402 | 1.19 | >4.0 | >10 |
| Terry cloth 100% Cotton | 1.40 | kill all | >10 |
| Control Cotton cloth #400 | / | all grow | all grow |

Example V This example illustrates the quantitative antibacterial study (AATCC Test Method 100) of Anti-1 finished fabrics.

Quantitative studies of biocidal properties of the Anti-1 finished fabrics indicates that even at a very low concentration of the finishing bath, biocidal properties on fabrics can be obtained. AATCC Test Method 100 was adopted in this study. According to this test method, four pieces of staked circular fabric swatches 4.8±0.1 (about one grams) were inoculated with 1.0±0.1 milliliter of inoculum in a 250 milliliter jar. The inoculum was a nutrient broth culture containing over $1.0 \times 10^6$ clone forming units (CFU) of organisms. After the swatches were inoculated, they were neutralized by 100 milliliter of a 0.02% sodium thiosulfate solution in the jar. The contact time was the time between inoculation and neutralization. The jar was vigorously shaken and the neutralized solution was diluted in serial. The dilutions, usually 100, 101, and 102, were plated on nutrient agar and incubated for 18–24 hours at 37° C. The number of bacteria recovered from the inoculated finished fabrics was counted and compared with that from untreated fabrics. Six log reduction means the total inactivation of bacteria, and one log reduction means that finished fabrics reduced bacteria counts from 106 CFU to 105 CFU.

Finished fabrics prepared from solutions containing 1%–6% of monomethylol-5,5-dimethylhydantoin following the protocol set forth in Example 1 with pickup rates below 1% have been tested. The biocidal properties of such fabrics are set forth in Table III.

TABLE III

Effects of Finishing Concentrations of Anti-1 on Bacterial Reduction Rates.

| Conc. of agent Anti-1 | Material | Take up % | Bacterial reduction rates on contact time | | | | | |
|---|---|---|---|---|---|---|---|---|
| | | | 0 min | | 30 min | | 60 min | |
| | | | *E. coli* | *S. aureus* | *E. coli* | *S. aureus* | *E. coli* | *S. aureus* |
| 1% | #400 | 0.65 | No | No | No | 1 log | No | No |
| | #7402 | 0.14 | No | No | 1 log | No | 1 log | No |
| 2% | #400 | 0.03 | No | 1 log | 6 log | 6 log | 6 log | 6 log |
| | #7402 | 0.07 | No | No | 6 log | 1 log | 6 log | 6 log |
| 4% | #400 | 0.47 | 6 log | 6 log | 6 log | 6 log | 6 log | 6 log |
| | #7402 | 0.45 | 6 log | 6 log | 6 log | 6 log | 6 log | 6 log |
| 6% | #400 | 0.70 | 6 log | 6 log | 6 log | 6 log | 6 log | 6 log |
| | #7402 | 0.70 | 6 log | 6 log | 6 log | 6 log | 6 log | 6 log |

400 is 100% cotton plain woven fabric and #7402 is a 65/35 polyester/cotton plain woven fabric. Six log reduction means total kill.

Table IV shows the effects of chlorine concentrations on biocidal properties of the antibacterial fabrics finished using the protocol set forth in Example 1. Every cycle of regeneration with different concentrations of chlorine will result in slight damages to the grafted heterocyclic rings. A concentration of 4% of monomethylol-5,5-dimethylhydantoin was selected as the finishing bath, and the take-up rate of the Anti-1 was 1.29%. The results obtained show some unexpected results for the #7402 fabric, which has more durable biocidal properties than cotton fabrics. Regeneration of the biocidal properties with lower chlorine concentration is preferred.

TABLE IV

Effects of Chlorine Concentration on Biocidal Properties (Bacterial Reduction Rates)

| Cl % | Fabric | After five Washings | | After ten Washings | | After fifteen washings | | After twenty washings | |
|---|---|---|---|---|---|---|---|---|---|
| | | E. coli | S. aur. | E. coli | S. aur. | E. coli | S. aur. | E. coli | S. aur. |
| 0.01 | #400 | 6 log | 6 log | 6 log | 6 log | 6 log | 6 log | 6 log | 6 log |
| | #7409 | 6 log | 6 log | 6 log | 6 log | 6 log | 6 log | 6 log | 6 log |
| 0.1 | #400 | 6 log | 6 log | 6 log | 6 log | 6 log | 6 log | 1 log | 0 log |
| | #7409 | 6 log | 6 log | 6 log | 6 log | 6 log | 6 log | 6 log | 6 log |
| 0.25 | #400 | 6 log | 6 log | 2 log | 0 log | 1 log | 0 log | 1 log | 0 log |
| | #7409 | 6 log | 6 log | 6 log | 6 log | 6 log | 6 log | 1 log | 1 log |

400 is 100% cotton and #7409 is a 65/35 polyester/cotton blend. Contact time=60 min. Six log reduction means total kill of bacteria. Zero log reduction means some reduction of bacterial growth and extended contact causes further reduction. Washing tests were following AATCC-124 using machine washing warm (140° C.) for 15 min. and 90 grams of AATCC detergent 124.

Example VI

This example illustrates the quantitative antibacterial study (AATCC Test Method 100) of Anti-2 finished fabrics.

Fabrics finished in accordance with the protocol set forth in Example II with Anti-2, i.e., 1,3-dimethylol-5,5-dimethylhydantoin, were also tested with AATCC test method 100, which was briefly described in Example IV. In the tests, a diluted CLOROX® solution containing 0.01 % active chlorine was used to chlorinate the finished fabrics. The biocidal properties of Anti-2 finished fabrics are set forth in Table V.

Example VII

This example illustrates the durable press properties of Anti-2 finished fabrics.

Fabrics finished with Anti-2 in accordance with the protocol set forth in Example II also exhibit durable press properties, which is understandable because the structure of DMDMH is very similar to that of 1,3-dimethylol-4,5-dihydroxylethylene urea (DMDHEU). Durable press properties were tested according to AATCC Test Method 66. In the tests, six warp specimens and six filling specimens of #400 cotton fabrics having the size of 15×40 mm were conditioned in a conditioning room (21±1° C. and 65±2% relative humidity) for over 24 hours. The wrinkle recovery angles of twelve samples which were creased with three

TABLE V

Durable Antibacterial Properties of Anti-2 Finished Fabrics

| Conc of Anti-2 | Fabric | After five washes | | After ten washes | | After fifteen washes | | After twenty washes | | After twenty washes | |
|---|---|---|---|---|---|---|---|---|---|---|---|
| | | E. coli | S. aur. | E. coli | S. aur. | E. coli | S. aur. | E. coli | S. aur. | E. coli | S. aur. |
| 2% | #400 | 6 log | 6 log | 6 log | 6 log | 6 log | 6 log | 6 log | 6 log | 6 log | 6 log |
| | #7409 | 6 log | 6 log | 6 log | 6 log | 6 log | 6 log | 6 log | 6 log | 6 log | 6 log |
| 6% | #400 | 6 log | 6 log | 6 log | 6 log | 6 log | 6 log | 6 log | 6 log | 6 log | 6 log |
| | #7409 | 6 log | 6 log | 6 log | 6 log | 6 log | 6 log | 6 log | 6 log | 6 log | 6 log |
| 10% | #400 | 6 log | 6 log | 6 log | 6 log | 6 log | 6 log | 6 log | 6 log | 6 log | 6 log |
| | #7409 | 6 log | 6 log | 6 log | 6 log | 6 log | 6 log | 6 log | 6 log | 6 log | 6 log |

400 is 100% cotton and #7409 is a 65/35 polyester/cotton blend. Contact time=60 min. Six log reduction means total kill of bacteria. Zero log reduction means some reduction of bacterial growth and extended contact causes further reduction.

warp and filling specimens on face side and three warp and filling specimens on back side were measured. Table VI shows the average wrinkle recovery angles of the finished fabrics after repeated washings. With higher concentration

TABLE VI

Wrinkle Recovery Angles of Anti-2 Finished #400 Pure Cotton Fabrics

| | Average Wrinkle Recovery Angle (degree) | | | | | | |
|---|---|---|---|---|---|---|---|
| Conc. of Anti-2 | Before washing | After 5 washing | After 10 washing | After 15 washing | After 20 washing | After 25 washing | After 30 washing |
| 0 | 87.0 | / | / | / | / | / | / |
| 2% | 88.3 | 97.2 | 100.4 | 96.0 | 97.8 | 103.0 | 99.2 |
| 6% | 115.4 | 111.8 | 108.4 | 111.2 | 111.0 | 111.2 | 109.8 |

TABLE VI-continued

Wrinkle Recovery Angles of Anti-2 Finished #400 Pure Cotton Fabrics

| | Average Wrinkle Recovery Angle (degree) | | | | | | |
|---|---|---|---|---|---|---|---|
| Conc. of Anti-2 | Before washing | After 5 washing | After 10 washing | After 15 washing | After 20 washing | After 25 washing | After 30 washing |
| 10% | 120.0 | 117.8 | 114.8 | 112.1 | 114.8 | 113.8 | 112.7 |

Washing conditions were same as that in Example III and Example V.

Example VIII

This example illustrates the effects of pH and dipping time on biocidal activity.

Based on the proposed reaction mechanism, the modification reaction, i.e., the coupling reaction, prefers acidic conditions. As such, a lower pH is generally preferred during the finishing process. The reaction time also has an effect on the results of the chemical modification. The reaction time and pH values of finishing solutions were varied. Acidic conditions with lower pH values increased the pick-up rate of finishing agent by the finished fabrics, a finding which is consistent with the expected reaction mechanism. For instance, lowering the pH from 4.6 to 2.5 almost doubled the pick-up rates (Table VII). However, extended reaction times do not have any significant effect on the yields of the finishing fabrics.

TABLE VII

Biocidal Properties of Cotton Fabrics Processed Under Different pH's and Dipping Times

| pH | Dipping Time (min) | Pick-up rate % | Biocidal result against *E. Coli* after 1st wash | after 5 or 8 washes |
|---|---|---|---|---|
| 2.50 | 30 | 2.83 | >5 mm | kill all |
| 4.65 | 30 | 1.42 | >2 mm | >3 mm |
| 2.47 | 5 | 2.88 | >1 mm | kill all |
| 4.56 | 5 | 1.64 | >2 mm | >3 mm |

In addition, the finished fabrics were also tested in extensive washing tests. Generally, after 5–8 times of machine-washing according to AATCC Test Method 124, the fabrics were recharged with chlorine bleach and were tested against the bacteria. The disinfection distances of the samples still indicated that the fabrics finished under lower pH have strong bactericidal abilities.

Example IX

This example illustrates the breaking strength of the finished fabrics treated with Anti-1.

Table VIII indicates the breaking strength retention of the Anti-1 finished fabrics after extensive washes and regenerations of biocidal properties with different chlorine concentrations. The fabrics were finished in a solution with a concentration of 4% of monomethylol-5,5-dimethylhydantoin, and the take-up rate of the Anti-1 on the fabrics was 1.29%. Washing conditions were the same as in Table IV. Tensile strength of the fabrics were tested following American Society for Testing and Materials (ASTM) test method D1682. In the tests, a number of ravelled specimens with their long dimension parallel to filling of the fabrics was prepared in size of 25.4 mm×152.4 mm. Then, breaking load of the fabrics was recorded in pound (lb).

TABLE VIII

Breaking Strength Retention of Some Anti-1 Finished Fabrics

| | | | Breaking Strength, lb (% retention) | | | | | |
|---|---|---|---|---|---|---|---|---|
| Cl % | Fabric | Before | After treatment | After Bleach | After 5 washes + Bleach | After 10 washes + Bleach | After 15 washes + Bleach | After 20 washes + Bleach |
| 0.01 | #400 | 31.75 | 24.30 (77%) | 23.43 (74%) | 23.27 (73%) | 20.14 (63%) | 20.35 (64%) | 19.46 (61%) |
| | #7509 | 30.71 | 32.27 (100%) | 33.00 (100%) | 32.41 (100%) | 31.16 (100%) | 31.80 (100%) | 32.06 (100%) |
| 0.1 | #400 | 31.75 | 24.30 (77%) | 22.75 (74%) | 22.47 (74%) | 19.63 (62%) | 20.00 (63%) | 19.45 (61%) |
| | #7409 | 30.71 | 32.27 (100%) | 33.72 (100%) | 32.75 (100%) | 31.82 (100%) | 31.80 (100%) | 31.86 (100%) |
| 0.25 | #400 | 31.75 | 24.30 (77%) | 22.30 (70%) | 19.32 (61%) | 19.25 (61%) | 20.32 (64%) | 18.04 (60%) |
| | #7409 | 30.71 | 32.27 (100%) | 32.83 (100%) | 33.34 (100%) | 33.75 (100%) | 32.38 (100%) | 31.46 (100%) |

Example X

This example illustrates the preparation and testing of biocidal wood and other cellulose-containing materials:

I. Preparation of Wood Boards:

The blocks were prepared by dividing large cutting boards into squares with sides measuring 5 cm using a table saw. The blocks were of the face-grain configuration. The edges were then smoothened with 120 or 180 grit sandpaper as needed to achieve uniformity among all blocks. The blocks were visually inspected to be the correct size and any blocks that appeared to deviate from the standard were remeasured and discarded if they were an incorrect size.

The blocks (Bemis Manufacturing Company, 300 Mill Street, PO Box 901, Sheboygan Falls, Wis., 53085-0901) were labeled based on concentration and ascending numbers. The blocks were immersed in solutions containing the following two formulations, respectively:

|  | #1 | #2 |
| --- | --- | --- |
| DMDMH | 5% | 10% |
| $MgCl_2$ | 1% | 2% |
| Triton X-100 | 0.1% | 0.1% |

And the blocks were taken out from the solutions after they are completely soaked by the chemicals, and then dried at 80° C. in an oven for a prolonged time till they are completely dry. The curing of the blocks was conducted at 150° C. for over 30 minutes.

II. Activation of the Blocks:

A bleach process is necessary to activate the biocide. A bleach solution containing about 0.05% sodium hypochlorite was prepared from a commercial Clorox liquid (containing 5.25% sodium hypochlorite). The volume of the solution was based on a liquid to wood mass ratio of 50:1. The blocks were scrubbed lightly on a sponge saturated with the chlorine solution from the bath for five strokes. The blocks were placed face down in the diluted bleach solution for 15 minutes. After 15 minutes the blocks were transferred directly to a cooling rack (to allow even drying) in a laminar flow hood that had been previously sterilized with a 70% ethanol solution and left with the exhaust turned on. The blocks were then left in the laminar flow hood until completely dry (at least five hours).

III. Testing of the Blocks.

1. A sample of *E. coli* enhanced green fluorescent protein (B)GFP 0157:H7 was inoculated into a test tube of LB broth with 0.01% ampicillin and 0.01% novobiocin antibiotics (to be referred to as LBAN). The test tube was labeled and then incubated at 37° C. for 24 hours. The sample was then serial diluted with LBAN broth. 0.1 mL of the broth was then inoculated onto LB or Brain Heart Infusion (BHI) agar, also with ampicillin and 0.01% novobiocin antibiotics. The concentrations of $10^{-7}$, $10^{-6}$, and $10^{-5}$ were spread plated. These plates were allowed to incubate for 24 hours at 37° C. The CFU/mL was determined by averaging the colonies from the plates of the most easily countable concentration.
2. A bucket of ice was used so that the inoculum could be kept in the stationary phase during the length of the experiment.
3. The agar plates were removed from the 4° refrigerator and dried in the incubator upside down with the lid slightly ajar to allow excess water to evaporate. The plates were dried for 15 minutes and then labeled numerically.
4. The blocks were stacked in the laminar flow hood so that they were in the order they were to be inoculated.
5. The order of the blocks was transcribed so that the numbers on the plates would correspond to the correct block.
6. The inoculum was vortexed for several seconds and then placed in the ice bath.
7. The timer was started and the inoculum was spread on the blocks at the rate of one per 30 seconds.
8. 0.2 mL of the inoculum was spread onto the blocks using the pipet tip and pipetter. A new pipet tip was used for each block.
9. After the correct (variable) contact time, the blocks were carefully pressed on the agar surface for 20 seconds and then the plates were inverted and placed in an incubator at 37° C. for 24 hours.
10. The colonies were counted for each plate and thus the kills were determined for each concentration.
11. The inoculum was vortexed for each block.

| Data and Observations: | | | |
| --- | --- | --- | --- |
| | | Treatment | |
| | None | 5%* | 10%* |
| *A* | | | |
| Inoculum $2.5 \times 10^5$ | 884 ± 232 Contact time 5 minutes | 125.3 ± 74.1 (85.0%)** | 166.3 ± 132.2 (81.2%)** |
| *B* | | | |
| Inoculum $1.8 \times 10^5$ | 475.3 ± 76.6 Contact time 5 minutes | 11.6 ± 11.4 (97.6%) | 26.3 ± 27.6 (94.5%) |
| *C* | | | |
| Inoculum $1.4 \times 10^5$ | 446 ± 8.5 Contact time 5 minutes | 65 ± 23.5 (85.4%) | 48 ± 44.2 (89.2%) |
| *D* | | | |
| Inoculum $1.4 \times 10^5$ | 394.3 ± 78.4 Contact time 5 minutes | 19.8 ± 6.8 (95.0%) | 26.8 ± 20.1 (93.2%) |
| *E* | | | |
| Inoculum $1.0 \times 10^4$ | 106.5 ± 9.2 Contact time 5 minutes | 2.5 ± 2.9 (97.7%) | 2.3 ± 3.4 (97.8%) |
| *F* | | | |
| Inoculum $1.0 \times 10^4$ | 456.8 ± 38.6 Contact time 5 minutes | 25.9 ± 13.8 (94.3%) | 31.7 ± 25.1 (93.1%) |
| *G* | | | |
| Inoculum $3.3 \times 10^4$ | 204.5 ± 12.0 Contact time 2.5 minutes | 20.8 ± 13.8 (89.8%) | 10.3 ± 7.8 (95.0%) |
| *H* | | | |
| Inoculum $3.3 \times 10^4$ | 73.5 ± 10.6 Contact time 5 minutes | 14 ± 11.4 (80.1%) | 7.4 ± 4.0 (89.9%) |
| *I* | | | |
| Inoculum $1.0 \times 10^4$ | 47 ± 5.8 Contact time 5 minutes | 12.3 ± 8.4 (73.8%) | 6 ± 4.2 (87.2%) |
| *J* | | | |
| Inoculum $1.37 \times 10^5$ | 328.3 ± 46.0 | 63.7 ± 45.1 (80.6%) | 37.9 ± 14.3 (88.5%) |
| | 323.5 ± 94.0 | 45.8 ± 19.2 (85.8%) | 14.6 ± 12.5 (95.5%) |

-continued

Data and Observations:

| | | Treatment | |
|---|---|---|---|
| | None | 5%* | 10%* |
| | Contact time 5 minutes | 37.4 ± 15.8 | 29.7 ± 25.1 |

K

| | | | |
|---|---|---|---|
| Old Blocks | 52.8 ± 14.5 | 12.0 ± 9.4 (77.3%) | 9.3 ± 5.4 (82.4%) |
| New Blocks Inoculum 1.2 × 10$^4$ | 83.0 ± 67.3 Contact time 5 minutes | 7.7 ± 3.0 (90.7%) | 4.9 ± 5.8 (94.1%) |

L

| | | | |
|---|---|---|---|
| Old Blocks | 11.7 ± 3.1 | 1.3 ± 1.3 (88.9%) | 0.67 ± 0.71 (94.3%) |
| New Blocks Inoculum 8.0 × 10$^1$ | 9 ± 11.2 Contact time 5 minutes | 0.17 ± 0.41 (98.1%) | 0 ± 0 (100%) |

M

| | | | |
|---|---|---|---|
| Old Blocks | 18.7 ± 2.9 | 3.3 ± 2.1 (82.4%) | 3.3 ± 2.4 (82.4%) |
| New Blocks Inoculum 6.45 × 10$^3$ | 8.3 ± 1.5 Contact time 10 minutes | 3.3 ± 2.4 (60.2%) | 1.6 ± 1.8 (80.7%) |

N

| | | | |
|---|---|---|---|
| Old Blocks | 152.8 ± 41.1 | 20.7 ± 6.1 (86.5%) | 15.9 ± 6.7 (89.6%) |
| New Blocks Inoculum CFU/mL 6.6 × 10$^4$ | 151.3 ± 64.7 Contact time 10 minutes | 17.8 ± 4.8 (88.2%) | 6.2 ± 5.8 (95.9%) |

*Concentration of the biocide that was applied to the blocks
**means CFU/block ± standard deviation (percentage reduction compared to control).
***Old blocks refer to the blocks that were already in use for this experiment, new blocks refer to fresh blocks that were now just beginning to be used.

Figure 3A:
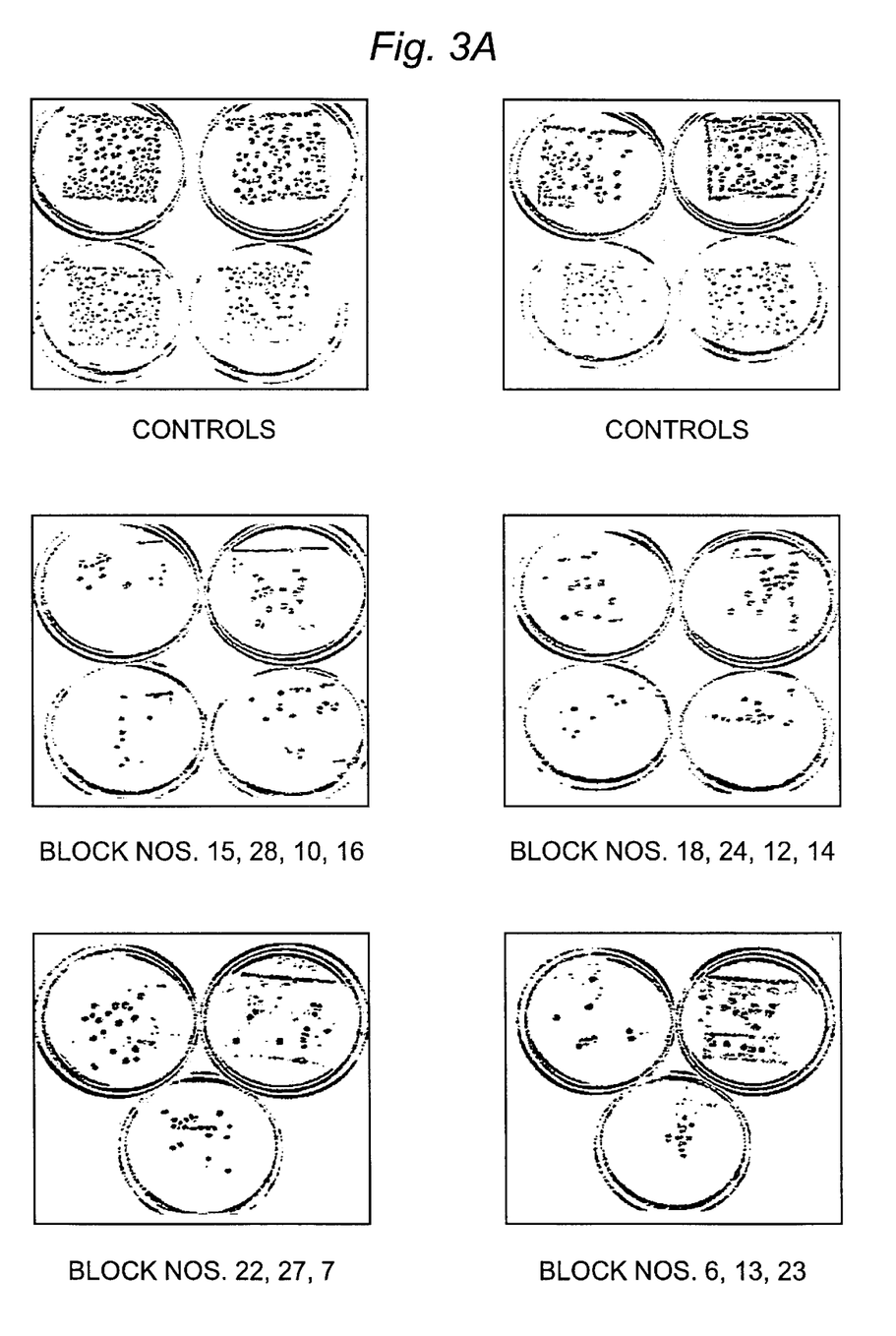
Figure 3B:
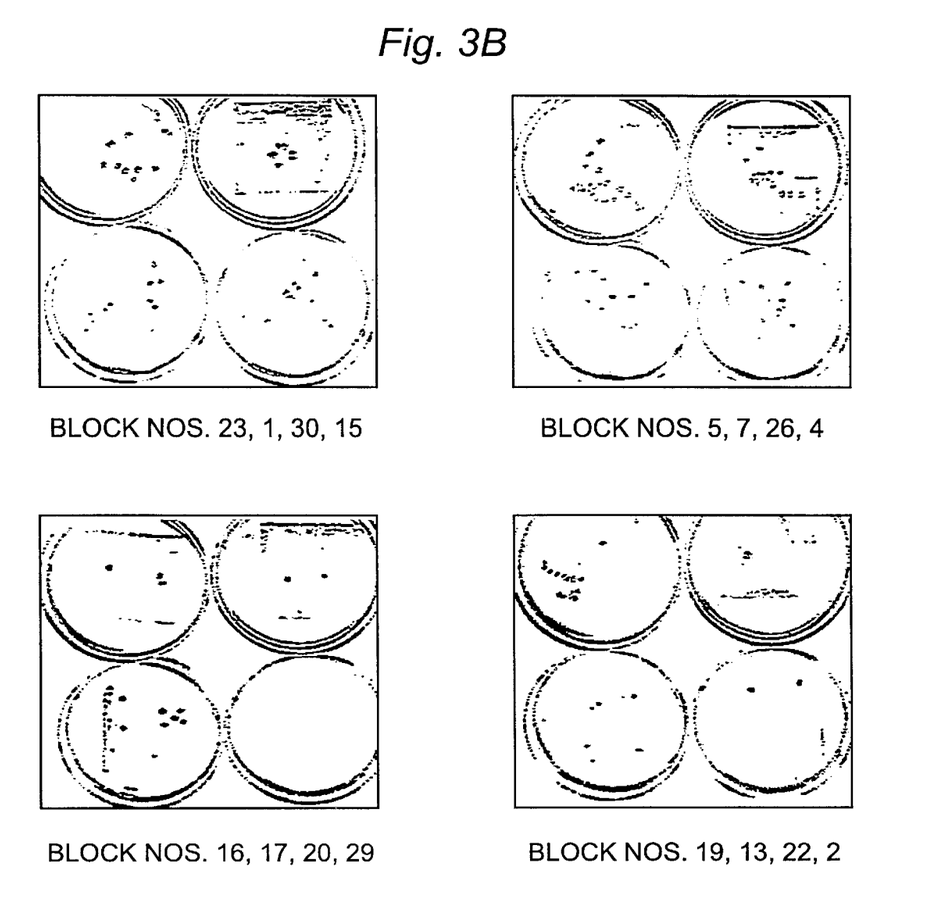

FIGS. 3 A–B illustrate the relative amount of CFU recovered from the blocks in Sample N. From the data, it can be estimated that the average percent reduction of bacterium on the 5% blocks as compared to the untreated control blocks was about 86%. For the 10% concentration blocks, the reduction is 91%. Clearly, the concentration of the biocide on the blocks is the strongest contributor to bacterial reduction. Contact time does not appear to play a major role in the % reduction, as noted in trial H in which bacterium concentration was kept constant while the contact time was varied between 2.5 minutes and 5 minutes. It should be noted on this trial that although less CFU were recovered as time increased, the percent recovery went down. This can largely be attributed to the drying effect on bacterial viability, and also may suggest that the biocide works very fast, and does most of it's killing within a very short time.

As illustrated in trials J–N, the newer blocks had more effective reductions of the bacterium typically by 5–10%. However, it should be noted that the new blocks were only compared with more used blocks on a limited basis.

Example XI

This example further illustrates the preparation and testing of biocidal wood and other cellulose-containing materials:

This example consisted of bacterial challenge studies of wood blocks treated and untreated with N-heterocyclic amines.

I. Bacterial cultures: Overnight (at 37° C.) cocktail cultures of *Escherichia coli* O157:H7, *Salmonella typhimurium*, and *Listeria monocytogenes* Scott A (provided by K.A. Glass, Food Research Institute, UW-Madison) were used. They were grown in nutrient broth (Difco, Detroit, Mich.). Bacteria were inoculated onto the surface by depositing 0.5 mL of the culture (at 105 to 109 CFU/25 cm$^2$ area) and spread evenly with a 1 mL disposable pipette tip. For plate counts, nutrient agar plates (Difco, 1.5% agar) were used.

II. Contact Surfaces: Treated and untreated (control) wooden cutting boards were tested. These blocks were cut into 5×5×2.5 cm size (face area 25 cm$^2$), exposed to UV light for 12 h, and additionally microwaved (at 800 W) for 60 s to disinfect the surface and interior before inoculation (Park and Cliver, 1996).

Figure 4A:
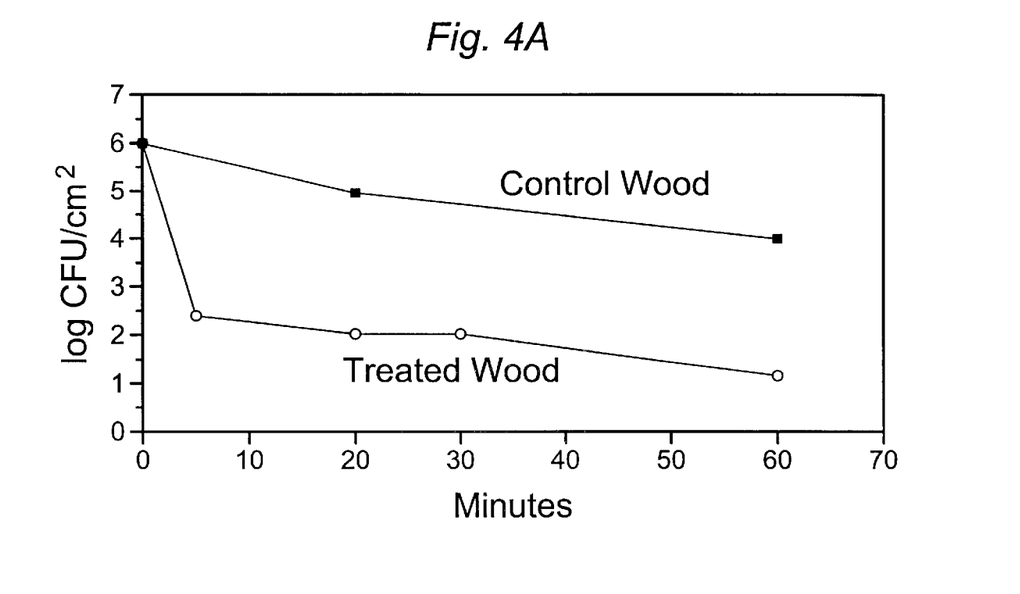
Figure 4B:
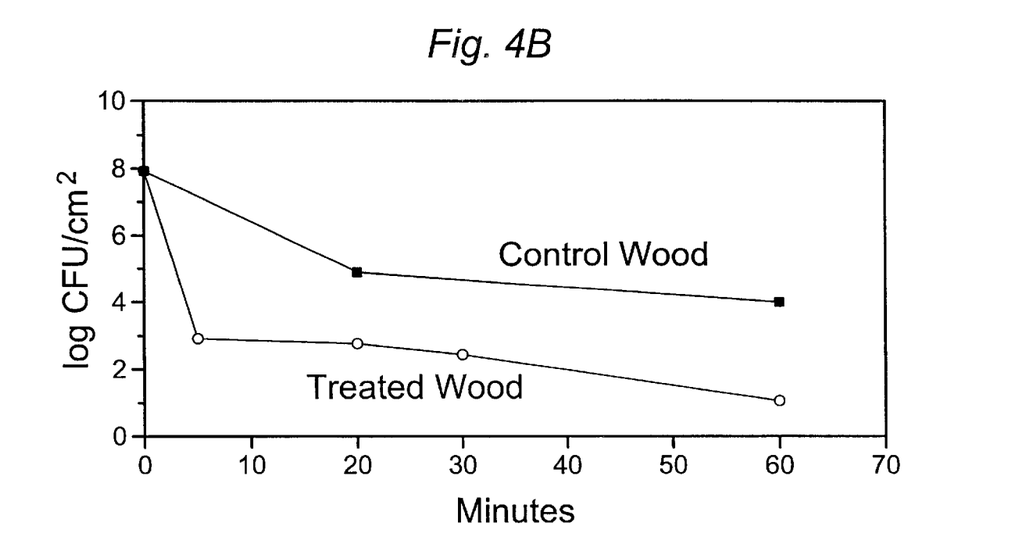

III. Results At 10$^{4-5}$ bacterial level, the treated wood cutting boards can exhibit a complete reduction of *E. coli* O157:H7on the surfaces. At 10$^6$ bacteria level (FIG. 4A), 4 logs are killed within the first 5 minutes on the treated wood surface. At 10$^8$ level (FIG. 4B), a 6 log kill is achieved within the first 1 h. These results are repeatable after a chlorine bleach wash (for reactivation) of the wood even after 12 assays indicating that the antibacterial compound was very stable. Activity was not species specific; gram positive and negative organisms were killed equally.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A cellulose based composition, said composition comprising:
    a cellulosic material, wherein said cellulosic material is a wood material selected from the group consisting of a wood, wood fabric and a wood pulp; and
    a heterocyclic N-halamine covalently attached to said material.

2. The composition of claim 1, wherein said wood material is a food contact surface.

3. The composition of claim 2, wherein said food contact surface is a member selected form the group consisting of a plate, cookware, cutlery, a knife, a spoon, a cup, a table, a cutting board, a meat block, a baker's top, a counter top, kitchen ware, and a floor.

4. The composition of claim 3, wherein said food contact surface is a cutting board.

5. The composition of claim 1, wherein said cellulosic material is fabricated into a diaper, napkin, a table cloth, a bandage, and a gauze.

6. The composition of claim 1, wherein said heterocyclic N-halamine is a halogenated product of a member selected from the group consisting of monomethylol-5,5-dimethylhydantoin (MDMH), 1,3-dimethylol-5,5-dimethylhydantoin (DMDMH); monomethylolated and dimethylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid and 5,5-dimethylhydantoin; and monomethoxylated and dimethoxylated derivatives of monomethylolated and dimethylolated derivatives of 6,6-dimethyl-1,3,5-triazine-2,4-dione, 4,4,5,5-tetramethyl-1,3-imidazolidin-2-one, cyanuric acid, 5,5-dimethylhydantoin, 2,2,5,5-tetramethyl-1,3-imidazolidin-4-one and mixtures thereof.

7. The composition of claim 6, wherein said heterocyclic N-halamine is a halogenated product of a member selected from the group consisting of either monomethylol-5,5-dimethylhydantoin (MDMH) and 1,3-dimethylol-5,5-dimethylhydantoin (DMDMH).

8. A process for making a cellulosic material a biocidal article, said process comprising:
 (a) immersing said cellulosic material in an aqueous treating solution which comprises a catalyst, a wetting agent and a heterocyclic amine, wherein said cellulosic material is a wood material selected from the group consisting of a wood, wood fabric and a wood pulp; and
 (b) treating said cellulosic material with a halogenated aqueous solution, thereby rendering said cellulosic material a biocidal article.

9. The process of claim 8, further comprising removing excess aqueous treating solution from said cellulosic material before treating said cellulosic material with a halogenated aqueous solution.

10. The process of claim 9, further comprising drying said cellulosic material after removing excess aqueous treating solution to produce a dried cellulosic material.

11. The process of claim 10, further comprising curing said dried cellulosic material to produce a cured cellulosic material.

12. The process of claim 11, further comprising washing said cured cellulosic material to remove excess reagents.

13. The process of claim 12, further comprising drying said washed cellulosic material to remove water.

14. The process of claim 8, wherein said wood material is a food contact surface.

15. The process of claim 14, wherein said food contact surface is a member selected form the group consisting of a plate, cookware, cutlery, a knife, a spoon, a cup, a table, a cutting board, a meat block, a baker's top, a counter top, kitchen ware and a floor.

16. The process of claim 8, wherein said cellulosic material is fabricated into a member selected from the group consisting of a diaper, napkin, a table cloth, a bandage, and a gauze.

17. The process of claim 15, wherein said food contact surface is a cutting board.

18. The process of claim 8, wherein said biocidal article is a biocidal food contact surface.

19. The process of claim 17, wherein said heterocyclic amine is a member selected from the group consisting of monomethylol-5,5-dimethylhydantoin (MDMH), 1,3-dimethylol-5,5-dimethylhydantoin (DMDMH); monoalkylolated and dialkylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid and 5,5-dimethylhydantoin; and monoalkoxylated and dialkoxylated derivatives of monoalkylolated and dialkylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid, 5,5-dimethylhydantoin, 2,2,5,5-tetramethyl-1,3-imidazolidin-4-one and mixtures thereof.

20. The process of claim 19, wherein said heterocyclic N-halamine is a halogenated product of a member selected from the group consisting of either monomethylol-5,5-dimethylhydantoin (MDMH) and 1,3-dimethylol-5,5-dimethylhydantoin (DMDMH).

21. A cellulose based composition selected from the group consisting of a wood, a wood fabric and a wood pulp, said composition comprising:
 a cellulosic material, wherein said cellulosic material is a cellulosic-polyester blend; and
 a heterocyclic N-halamine covalently attached to said material.

* * * * *